United States Patent
Hajnal et al.

(10) Patent No.: US 9,839,607 B2
(45) Date of Patent: Dec. 12, 2017

(54) PH-DEPENDENT GRADUAL RELEASE PHARMACEUTICAL COMPOSITION

(75) Inventors: Péter Hajnal, Budapest (HU); Péter Szegó, Budapest (HU); István Nándor Antal, Budapest (HU); Judit Dredán, Budapest (HU); Imre Klebovich, Budapest (HU); Miléna Bea Lengyel, Budapest (HU)

(73) Assignee: Péter Hajnal, Budapest (HU)

( * ) Notice: Subject to any disclaimer, the term of this patent is extended or adjusted under 35 U.S.C. 154(b) by 1134 days.

(21) Appl. No.: 13/813,088

(22) PCT Filed: May 12, 2011

(86) PCT No.: PCT/HU2011/000047
§ 371 (c)(1),
(2), (4) Date: Apr. 4, 2013

(87) PCT Pub. No.: WO2012/013994
PCT Pub. Date: Feb. 2, 2012

(65) Prior Publication Data
US 2013/0195974 A1    Aug. 1, 2013

(30) Foreign Application Priority Data

Jul. 30, 2010 (HU) .................................... 1000407

(51) Int. Cl.
*A61K 9/00* (2006.01)
*A61K 9/50* (2006.01)
*A61K 33/00* (2006.01)
*A61K 47/32* (2006.01)

(52) U.S. Cl.
CPC .......... *A61K 9/0002* (2013.01); *A61K 9/5073* (2013.01); *A61K 9/5084* (2013.01); *A61K 33/00* (2013.01); *A61K 47/32* (2013.01); *A61K 9/5026* (2013.01); *A61K 9/5042* (2013.01)

(58) Field of Classification Search
None
See application file for complete search history.

(56) References Cited

U.S. PATENT DOCUMENTS

| | | | | |
|---|---|---|---|---|
| 3,121,663 A | * | 2/1964 | Parker | A61K 9/0007 424/436 |
| 4,289,750 A | * | 9/1981 | Kopp | A61K 33/00 424/451 |
| 5,102,668 A | * | 4/1992 | Eichel | A61K 9/1635 424/458 |
| 5,213,794 A | * | 5/1993 | Fritsch | A61K 9/2027 424/480 |
| 5,750,104 A | * | 5/1998 | Sipos | A61K 9/4808 424/94.21 |
| 6,368,629 B1 | * | 4/2002 | Watanabe | A61K 9/2826 424/468 |
| 7,438,929 B2 | * | 10/2008 | Beckert | A61K 9/2081 424/489 |
| 2002/0034541 A1 | | 3/2002 | Valducci | |
| 2006/0093670 A1 | | 5/2006 | Mizushima | |

FOREIGN PATENT DOCUMENTS

WO    2005/051348 A2    6/2005
WO    2010/096814 A1    8/2010

OTHER PUBLICATIONS

Breitkreuz et al.: "Enteric-coated solid dosage forms containing sodium bicarbonate as a drug substance: an exception from the rule?", Journal of Pharmacy and Pharmacology, 2007, vol. 59, No. 1, pp. 59-65.

* cited by examiner

*Primary Examiner* — Michael G Hartley
*Assistant Examiner* — Lance Rider
(74) *Attorney, Agent, or Firm* — Jason D. Voight

(57) ABSTRACT

The invention concerns a pH-dependent gradual sustained release composition for increasing the pH in the upper part of the small intestines. Particles of the composition are provided with a multilayer polymer coating of specific structure which ensures the gradual release of the active agent in the range of pH 4.5 to 5.5. A process for preparing said composition is also claimed.

13 Claims, 4 Drawing Sheets

PH-DEPENDENT GRADUAL RELEASE PHARMACEUTICAL COMPOSITION

Figure 1:
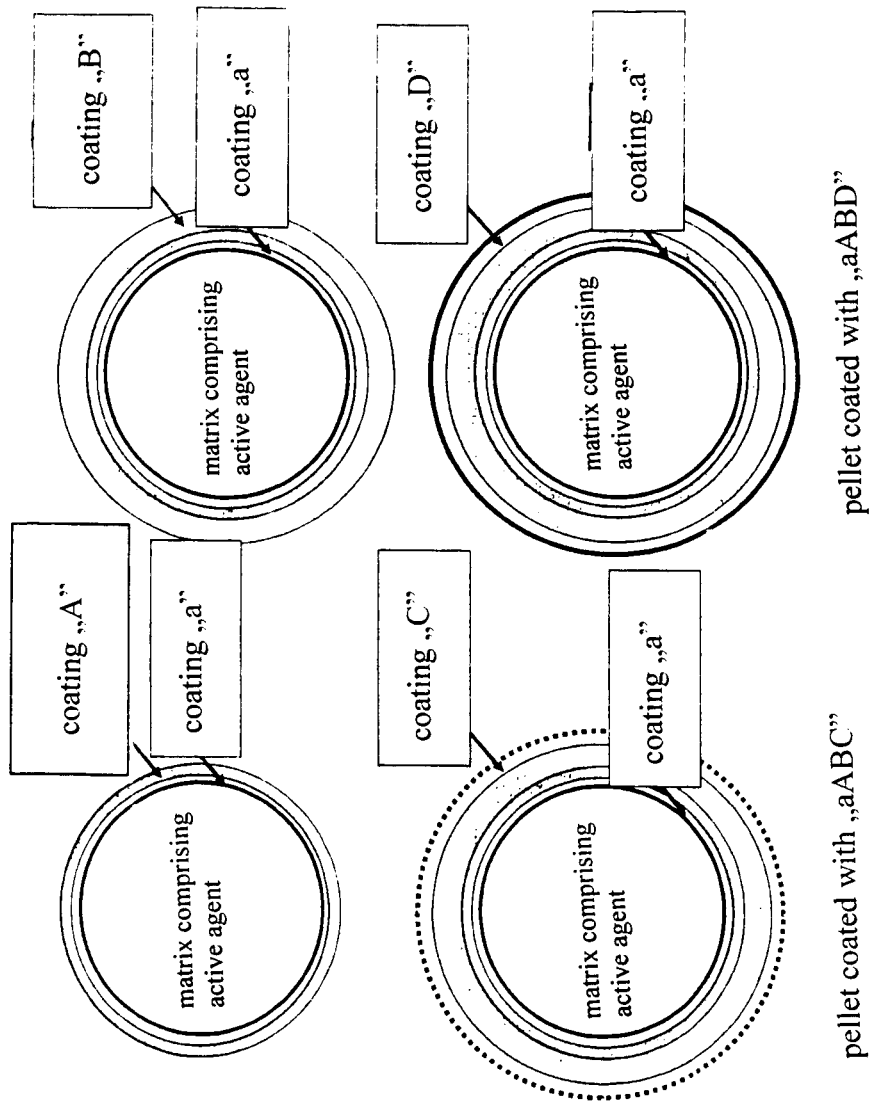

This is the national stage of International Application PCT/HU2011/000047, filed May 12, 2011.

The invention concerns a pH-dependent gradual sustained release pharmaceutical composition for increasing the pH in the upper part of the small intestine. Particles of the composition are provided with a multilayer polymer coating of specific structure, which ensures the gradual release of the active agent in the range of pH 4.5 to 5.5. A process for preparing said composition is also claimed.

BACKGROUND OF THE INVENTION

The acid-base balance of the body is an essential factor to the adequate regulation of metabolic processes, and the disturbance of this balance is frequently jeopardized by diseases as well as lifestyle habits of our age, for example stress, inappropriate nutrition, harmful practices and addictions.

A neutral or slightly alkaline pH is required in the duodenal lumen and in the further parts of the small intestine for many reasons.

For example the pH of the duodenal lumen or its change is a particularly important regulating factor of the gastric emptying, since the prolonged acid load of the duodenum delays emptying the food partly digested and converted into pulp in the stomach, i.e. the chymus, into the duodenum. The persistent prolongation of the approximately three-hour physiological gastric transit time causes disturbances in the motoric and secretory functions of the whole alimentary canal.

In addition, the optimum of the normal function of the approximately twenty "luminal" pancreatic digestive enzymes secreted into the duodenal lumen and present in the upper third of the small intestine, is in the pH range of 6.5 to 8.7, and orally added digestive enzymes also need this optimal chemical environment.

The inactivation of pepsins also takes place in the duodenal lumen at this pH, which is required to protect the small intestinal mucosa and the luminal pancreatic digestive enzymes.

Moreover, the alkaline environment promotes the emulsification of the lipid aggregates and the micelle-forming, the protection of the small intestinal mucosa, including the carbon dioxide/bicarbonate cycle, which takes place in the mucin layer adhered to the intestinal mucosa.

As it was mentioned above, this optimal pH environment promotes the adequate gastric motility and emptying, thereby alleviates the disturbances of the motoric and neuroendocrine-exocrine regulatory and secretory functions of the whole alimentary canal in various clinical scenarios.

Accordingly, the neutral or slightly alkaline pH range promotes the luminal phase digestion and food absorption, which may help to avoid the harmful effects caused by the huge amount of improperly digested food remained in the lumens of the small intestine and the colon as a consequence of the inadequate luminal digestion, which may contribute to the following clinical scenarios or cause transient or permanent disorders, for example:

Absorption disorders, deficiency diseases (vitamins, trace elements, etc.) and as a consequence, decline in the resistance of the organism, Increased osmotic pressure in the lumen of the small intestine and the colon, Allergic, cellular and humoral immunoreactions caused by improperly digested food fragments (peptides, hydrocarbons, etc.), Gastrointestinal disbacteriosis and absorption of toxic products caused by the condition, Increased intestine mucosal permeability, which promotes the absorption of toxic byproducts as well as immunoreactions, Irritation of the intestinal mucosa, Disturbance of the enterohepatic circulation of bile acids, abdominal complains caused by prolonged transit time and increased gas formation, for example discomfort, distention, pains, defecation complaints, etc.

It is important to note that the contradictions are negligible as compared to the scope of the indication field of bicarbonate, which contradictions are e.g. hypernatraemia, which is responsible to treatment, further, infrequent metabolic and respiratory alkalosis and respiratory acidosis.

If the acid-base balance of the gastrointestinal system is disturbed and the partially digested food mixed with gastric acid (gastric content or chymus) enters the duodenum without being neutralized, that is, without creating a near neutral or slightly alkaline gastric environment, the entering chymus makes the upper part of the small intestine acidic, which causes disturbances primarily in the digestion processes taking place in the duodenum, as mentioned above.

Earlier, these disturbances were treated for example by orally administered sodium bicarbonate (its exact chemical name: sodium hydrogen carbonate), i.e. by delivering it directly into the gastric lumen. In the present description sodium hydrogen carbonate is called sodium bicarbonate or simply bicarbonate in accordance with the therapeutic practice.

Bicarbonate and its metabolites, namely carbonic acid or carbon dioxide and water are essential and, within wide physiological ranges, not toxic elements of the vital processes.

Theoretically, bicarbonate can be used orally for the neutralization of the gastric acid or the acidic chymus, since the organism also uses bicarbonate secreted by the pancreas, the liver and the intestinal wall, for the neutralization of the gastric acid. However, under physiological circumstances, this process occurs primarily in the duodenum and the upper part of the small intestine rather than in the gastric lumen.

Owing to the absolute or relative bicarbonate deficit developed in the duodenal lumen for any reason (like transient or permanent deviations from a healthy lifestyle and functional disorders or diseases, parenchymal injuries) the duodenum/small intestine is subjected to an increased acid load.

In the point of view of the pharmaceutical technology, the per os use of sodium bicarbonate is challenging, because its dissolution have to be prevented in the gastric fluid, since the hydrochloric acid present in the stomach immediately neutralizes the bicarbonate, meanwhile gas develops, which causes tonicity and distension and may involve even greater risks in the case of a tense stomach or higher doses. For these reasons using bicarbonate in the stomach is contradicted, as mentioned above.

To avoid this, various enterosolvent bicarbonate containing compositions were developed. For example bicallorm tablets (Fresenius Medical Care Deutschland GmbH, Homburg, DE) and Nephrotrans capsules (Medice Arzneimittel Pütter GmbH & Co. KG, Iserlohn, DE) are on the market. In vitro modeling of the release of the active agent from these compositions and other compositions were disclosed by Breitkreutz at all ["Enteric-Coated Solid Dosage Forms Containing Sodium Bicarbonate as a Drug Substance: an Exception from the Rule?" JPP, 59: 59-65 (2007)].

The presently known compositions provided with enterosolvent coatings resist to the acidic environment and start to release the active agent at neutral or higher pH values. This effect is accomplished by the use of polymer coatings soluble above pH 6. Polymers applicable for this purpose are for example cellulose acetate, hydroxypropyl methylcellulose phthalate, carboxymethyl ethylcellulose, polyvinyl acetate phthalate and polymethacrylate.

Some of the pharmaceutical compositions disclosed in the literature release the active agent gradually, as they move along in the increasing pH environment of the intestines. However, these compositions also exert their effects above pH 6. For example in Patents CA2352496 and U.S. Pat. No. 7,022,345, respectively, Valducci disclosed oral pharmaceutical formulations showing pH-dependent multiphasic release of active agent Mesalazine.

The above-mentioned marketed enterosolvent pharmaceutical formulations release their active agents at neutral or basic pH values, that is, in the farther parts of the small intestine. Accordingly, they cannot be used for treating or preventing the harmful effects appearing in the duodenum and in the first part of the jejunum, such as digestive, functional, dyspeptic troubles, motility disorders and mucosal irritation.

The object of our work was to develop a pharmaceutical composition that resists to the highly acidic environment of the stomach, but is able to release its bicarbonate content in pH-dependent, gradual and sustained manner in slightly acidic environment, while moving on together with the intestinal content, thereby increasing the pH of the acidified parts of the intestines.

The considerable difficulty with coatings soluble in slightly acidic pH is however that the polymer coating begins to swell at a strongly acidic pH, and when moisture reaches the particle core, the pH on the surface of the alkaline active agent may locally exceed the lowest pH value at which the polymer is soluble, consequently, the coating starts to erode from inside, which leads to an early, uncontrolled and irreproducible release of the active agent.

Therefore it was a great challenge to elaborate the highly reproducible pharmaceutical composition according to the present invention.

General Description of the Invention

The invention concerns a pH-dependent gradual sustained release pharmaceutical composition usable for increasing the pH in the upper third of the small intestine.

The pharmaceutical composition according to the invention comprises at least a first and a second type of microparticles having multilayer enterosolvent coatings, the cores of the microparticles comprising sodium hydrogen carbonate and said multilayer coatings comprising at least a cationic polymer coating contacting the core, a pH-independent polymer coating and a pH-dependent soluble anionic polymer coating, wherein the coating of the first type of microparticles is resistant to acidic pH below a well defined first pH threshold value but disrupts above this pH threshold value, and the second type of microparticles is resistant to acidic pH below a well defined second pH threshold value but disrupts above this second pH threshold value, wherein said second threshold value is at least 0.5 pH unit higher than said first threshold value.

In a preferred embodiment the composition according to the present invention comprises microparticles provided with the coating layers shown in FIG. 1. Accordingly, the first type of microparticles comprises a cationic polymer coating insoluble above pH 5 (coating "a"),
a polymer coating soluble at pH≥6 (coating "A"),
a pH-independent polymer coating (coating "B") and
an anionic polymer coating soluble at pH≥4.5 (coating "C"), and the second type of microparticles comprises
a cationic polymer coating insoluble above pH 5 (coating "a"),
a polymer coating soluble at pH≥6 (coating "A"),
a pH-independent polymer coating (coating "B") and
an anionic polymer coating soluble at pH≥5.5 (coating "D").

Preferably, the coating layers of the microparticles according to the invention comprise the following polymers: coating "a" comprises an aminoalkyl methacrylate copolymer, coating "A" comprises a copolymer of methacrylic acid and methacrylate, coating "B" comprises a copolymer of ethyl acrylate and methyl acrylate, coating "C" comprises hydroxypropyl methylcellulose phthalate and coating "D" comprises a copolymer of methacrylic acid and ethyl acrylate.

In another preferred embodiment the ratio of the first and second types of microparticles of the composition according to the invention is 20/80 to 80/20.

In another preferred embodiment the composition according to the invention is filled in gastrosolvent capsules.

The invention also covers a process for the preparation of the composition according to the invention, which comprising preparing the particle cores from the active agent(s) and commonly used pharmaceutical additives using an alcoholic granulation process under anhydrous conditions, and applying the coating layers consecutively thereon, where coatings "a" and "A" are applied in the form of alcoholic solutions and coatings "B", "C" and "D" are applied in the form of aqueous solutions or dispersions. After that the various types of microparticles are mixed in a required ratio and optionally filled into gastrosolvent capsules.

DETAILED DESCRIPTION OF THE INVENTION

The invention concerns a composition usable for increasing the pH in the duodenum and the further parts of the small intestine, which composition starts to release the active agent at pH 4.5 in gradual, pH-dependent and sustained manner while passing through the intestines together with the intestinal content.

The above outlined features are implemented by a composition comprising microparticles having a particle core comprising sodium hydrogen carbonate provided with a multilayer coating, where the exterior layer provides the pH-dependent dissolution, the next layer provides the sustained release of the active agent and the innermost layer prevents the alkaline leaking, which could be caused by the moisture that reaches the alkaline content of the particle core and deteriorates the pH-sensitive layered coating from inside. The gradual release is achieved by particles having two types of coatings of pH-dependent solubility.

Contrary to the enterosolvent coatings commonly used in the medical practice, which are soluble in neutral or slightly alkaline conditions, the coatings according to the invention dissolve at weakly acidic pH values. As mentioned above, the difficulty with these coatings is that, as they get into the intestines from the highly acidic pH of the stomach, they begin to swell as the pH of the intestines slowly increases, which pH is still too acidic to disrupt the coating, but moisture can reach the particle core, and the bicarbonate present there starts to dissolve, which brings about an alkaline environment that erodes the coating from inside, which in turn leads to an early and uncontrolled release of bicarbonate.

The present invention is based on a composition usable for increasing the pH of the duodenum, which composition resists to a strongly acidic medium and is soluble in a weakly acidic medium, the microparticles of the composition are provided with a multilayer coating, wherein the undermost layer contacting the particle core is a polymer layer soluble in highly acidic medium and insoluble in alkaline medium, which polymer layer prevents the alkaline leakage from the particle core.

By the use of the composition according to the invention the alkali delivery into the stomach can be prevented and thus, it can exert its gastric acid neutralizing activity in the duodenum. Consequently, by the use of the composition according to the invention the bicarbonate deficit emerged in the duodenum can be alleviated right there, in the duodenal lumen, contrary to current practice.

Bicarbonate is an element of the carboxylic acid/carbon dioxide buffer system, which can be found in all cells of living organisms as well as in extracellular compartments, and thus, the compositions according to the invention can be used in broad therapeutic spectrum without side effects, time restrictions or interruption.

In a preferred embodiment, the core of the compound according to the invention is formed by solid granulated sodium bicarbonate particles having an average diameter of 0.8±0.2 mm.

The particle cores comprising bicarbonate are provided with a gastro-resistant pH-dependent soluble coating having a sandwich structure. The particles provided with the multilayer coatings according to the invention are hereinafter called micropellets or shortly, MPs.

The pH-dependent gradual release of the active agent is achieved by the simultaneous use of MPs having at least two types of multilayer coatings.

In the first step of this process, the release of bicarbonate starts from MP-4.5 into the duodenal lumen at pH 4.5, which is the first threshold value, and from that time on, it proceeds in a sustained manner and together with the bicarbonate secreted by the pancreas, the liver and the intestinal mucosa into the duodenal lumen, contributes to the alleviation of the acid load of the duodenum and subsequent regions of the small intestine according to the physiological processes, that is, to the increase of the pH of the lumens of the duodenum and subsequent regions of the small intestine.

In the clinical practice the release of bicarbonate at pH 4.5 involves novelty, since the gastro-resistant coatings of the presently used pharmaceutical compositions do not allow the active agents to dissolve in the duodenal lumen at a pH below 5.5. If the acid load is higher, these pharmaceutical compositions overpass the stomach as well as the duodenum without dissolution; the active agent is only released in the further parts of the small intestine, where the pH already increases under the effect of the intestinal juice.

FIG. 1 shows a preferred embodiment of the particles according to the invention. In this figure the structures of two types of MPs can be seen, where the first type of particles is provided with multilayer polymer coating "aABC". The average diameter of this particle is 0.9±0.2 mm and it dissolves at pH>4.5±0.1. The second type of particles is provided with multilayer polymer coating "aABD". The average diameter of this particle is 0.9±0.2 mm and it dissolves at pH>5.5±0.1.

Said coating layers are as follows. The first coating layer contacting the bicarbonate is polymer layer "a", which comprises a cationic polymer insoluble at pH>5. As it was discussed above, the function of this polymer is to insulate the enterosolvent coatings from the alkaline active agent of the core. Preferably, this cationic polymer is an aminoalkyl methacrylate copolymer, more preferably a copolymer composed of dimethylaminoethyl methacrylate and neutral methacrylic esters.

The second coating is polymer layer "A", which protects the MP from the penetrating moisture during the aqueous coating processes used in the application of the further layers. Preferably, coating "A" comprises an anionic copolymer based on methacrylic acid and ethyl acrylate.

The third coating is polymer layer "B", which provides pH-independent sustained release of the active agent. Preferably, coating "B" comprises a polyacrylate, more preferably it comprises a copolymer of ethyl acrylate and methyl acrylate.

In one of the particle types, the outermost, fourth coating of the MP is polymer layer "C", which is a gastro-resistant coating dissolving at pH>4.5±0.1, which ensures the pH-dependent release of the active agent. Coating "C" is preferably comprises hydroxypropyl methylcellulose phthalate. This type of particles is hereinafter called MP-4.5.

In the other particle type, the fourth coating is polymer layer "D". It is a gastro-resistant coating, which dissolves at pH>5.5±0.1. Accordingly, this coating enables the release of the active agent at a pH value different from, in particular higher than the above coating "C" does. Preferably, coating "D" comprises a copolymer of methacrylic acid and ethyl acrylate. This type of particles is hereinafter called MP-5.5.

As a consequence of the dissimilar dissolution pH ranges of coatings "C" and "D", respectively, a gradual release of the active agent takes place in the concomitance of MP-4.5 and MP-5.5.

In the first step the bicarbonate released from MP-4.5 into the duodenal lumen contributes to the alleviation of the acid load, that is, to the increase of the pH. When the duodenal environment reaches the threshold value of pH 5.5, the second component of the pharmaceutical composition, i.e. MP-5.5 starts to release bicarbonate in sustained manner. Thus, MP-5.5 augments the acid load alleviating effect of MP-4.5 and, acting jointly with the bicarbonate secreted into the duodenal lumen by the pancreas, the liver and the intestinal mucosa, they favorably contribute to the alleviation of the acid load of the duodenal lumen, that is, they further increase the pH in line with the physiologic process.

The first and the second components of the composition according to the invention, i.e. MP-4.5 and MP-5.5 are advantageously filled into gastrosolvent capsules. The components getting out of the capsules merge with the chymus gathered in the antrum. Owing to the gastro-resistant polymer coatings, however, they do not release the active agent there, but move together with the chymus into the duodenum continuously, depending on the gastric transit time, and exert their pharmacodynamic effect there, i.e. they neutralize the gastric acid or the chymus in the duodenum.

The ratio of the above-mentioned components can be adjusted in accordance with the condition to be treated. The ratio of MP-4.5/MP-5.5 can be for example 20/80, 40/60, 50/50, 60/40 or 80/20. By adjusting this ratio properly, the components advantageously complement each other's effect in the changing environment of the duodenum, providing the pH-dependent sustained release of the active agent, which enables individual treatment.

In view of the acid load caused by the acid and/or the acidic chymus emptying into the duodenum from the stomach, on the one hand, and the amount of bicarbonate secreted by the pancreas, the liver and the intestinal mucosa and available in the duodenum, on the other hand, the amount of bicarbonate dissolved from the composition according to the invention in the function of the pH can favorably be varied by adjusting the above-mentioned ratio of the components in accordance with the treatment of any specific disease developed for any reason, which caused the absolute or relative bicarbonate deficit in the duodenal lumen.

If the acid load of the duodenum/small intestine is permanently high, a higher MP-4.5/MP-5.5 ratio can be adjusted, thereby the composition can exert the acid load decreasing effect in the duodenum in the range of pH 4.5 to 5.5. Preferably, a lower MP-4.5/MP-5.5 ratio can be adjusted to avoid the delivery of the active agent content of MP-4.5 in the stomach, if the acid load of the duodenum/small intestine is not permanently high, but the amount of the bicarbonate secreted by the pancreas, the liver and the intestinal mucosa low in the duodenum for any reason.

Consequently, by varying the MP-4.5/MP-5.5 ratio in the composition according to the invention the consequences of the acid/alkaline disturbances developing in the lumen of the alimentary tract and primarily, the increased acid load developed in the duodenal lumen for any reason may be treated according to individual need.

When they are used orally, the compositions according to the invention deliver bicarbonate directly into the duodenal lumen and thus, they exert their activity according to the physiologic processes in the duodenum/small intestine lumen, i.e. the place where the bicarbonate deficiency appears, and they meet the bicarbonate need by adding bicarbonate. Thus, these compositions can advantageously be used in all clinical aspects, independently of the inducing factor, where the actual amount of the bicarbonate secreted in the lumen of the small intestine and present in the digestive juice is not enough to decrease or neutralize the acidity of the gastric acid or the chymus entering the lumen of the small intestine.

Correspondingly, the compositions according to the invention can be used for the treatment of the actual or permanent bicarbonate deficiencies of various extent, where the types of the bicarbonate deficiencies are as follows:

a) real bicarbonate deficiency originated from a failure of secretion (exocrine), b) relative bicarbonate deficiency, where the capacity of the bicarbonate secretion is in the physiological range and the efferent system is practically intact, but the neuro-hormonal regulation is disturbed, or the acid load is actually or permanently increased in the duodenal/small intestinal lumen.

Accordingly, the compositions according to the invention can advantageously be used to meet the bicarbonate need in the following clinical scenarios:

1) Real bicarbonate deficiency, which appears together with the various extents of the partial deficiencies of all the other components of the pancreatic digestive juice and thus, the composition according to the invention is indicated to be used in combination with pancreatic digestive enzymes added simultaneously, in the cases of:

chronic pancreatitis, extensive malignant and benign pancreatic tumors, autoimmune disorders of the pancreas and/or the liver, e.g. Sjögren syndrome, partial, external or partial, internal occlusions of the efferent duct systems of the pancreas and/or liver (external ones are e.g. by malignant/benign tumorous compression, scars, internal ones are e.g. stones, inflammation, parasites, mucus), abdominal surgical interventions (in the first place that of the stomach, the small intestine, the pancreas, the liver and the bile), hereditary pancreatic diseases, like the most frequent pancreatic cystic fibrosis.

The consequences of the deficiencies of the pancreatic digestive enzyme and bicarbonate, which appear concomitantly in the small intestinal lumen, are not only additive but also potentiate each other. When the neutralization of the chymus is incomplete due to the bicarbonate deficiency, and the luminal pH of the small intestine remains permanently lower, then even the activities of the pancreatic digestive enzymes present there ab ovo in lower amount decrease, since the acidic environment is not optimal for their activity. Further, they become irreversibly inactive under a given pH value (pancreatic lipase, pH<4). Because of the increased pH sensibility of the pancreatic lipase, the first noticeable symptom of the exocrine dysfunction of the pancreas is usually steatorrhea.

2) In the case of relative bicarbonate deficiency, for example the following diseases and conditions caused by lifestyle belong to the clinical scenarios:

Extremely increased acid load, which is perceivable in the case of the infrequent Zollinger Ellison syndrome (a tumor producing gastrin);

Increased acid load appearing in the small intestine temporarily or permanently and individually, which is caused by inadequate nutrition and lifestyle, like occasional or regular intake of increased amounts of over peppered food or unlimited consumption of alcohol, caffeine and nicotine, etc.;

Stress induces individually varying acid load in the small intestine through the direct brain-gut effect of the corticotropine releasing factor;

A slightly increased acid load of the small intestine often occur in diseases belonging to the indication field of gastric acid secretion inhibitors (H2RA, PPI), such diseases are for example:

duodenal ulcers, ventricular ulcers, peptic ulcers and erosions caused by non-steroid anti-inflammatory agents in the stomach and the duodenum, ulcers associated with Helicobacter pylori infection, oesophageal reflux, gastro-oesophageal reflux disease (GORD), (functional) dyspepsia associated with acid overproduction, etc, and in these cases, the doses of the gastric acid secretion inhibitors may optimally be decreased by making up the relative bicarbonate deficiency appearing in the duodenum according to individual needs, mainly during the maintenance treatment period, to avoid the possible side effects and to maintain an adequate gastric acid secretion rate, Motility disturbances of the upper gastro-intestinal tract, which are registered in all cases of peptic ulcers emerged for various reasons in the stomach and the duodenum, GORDs, functional dyspepsia, diabetes, where the acid load decreases under the effect of bicarbonate, consequently, the secretion of the hormones that delay the gastric emptying (e.g. secretin CCK, etc.) decreases as well, and thus, the aboral motility increases, which is favorable in all cases of reflux diseases (e.g. gastro-oesophageal, gastro-duodenal diseases);

In the case of diabetes mellitus, because of diabetes gastroparesis and the exocrine pancreas dysfunction often associated with diabetes, and maldigestion and secondary malabsorption;

In the case of functional dyspepsia (FD), where an objective "organic" injury of the alimentary system is not diagnostized, but the disturbance of the motility is established in each case, and the increased acid load of the duodenum can be shown in most cases, which is supported by the fact that hydrochloric acid added directly into the duodenum causes dyspeptic symptoms of healthy volunteers. The incidence rate of this clinical picture is rather high worldwide, that is, it affects more than 50% of the population temporarily or regularly.

The therapy of FD is presently empiric, and the efficiency of the applied therapies is not confirmed unambiguously. Thus, the compositions according to the invention can be used advantageously in the case of FD, since they can be used without risks. Their efficiency is also an important factor in diagnostic point of view. Further, it is unindifferent as to the medical costs considering the frequency of this clinical picture;

The treatment of the irritable bowel syndrome (IBS) is symptomatic; the alleviation of the acid load of the small intestine contributes to the increase of the pH dependent activities of the digestive enzymes secreted by the pancreas, that is, to the efficiency of the luminal digestion. Further, the adequate digestion in the small intestine exerts a beneficial effect on the transit times and the motility and, by acting upon the pathogenetic factors present behind the symptoms of IBS, contributes to the efficacity of the complex treatment. Moreover, the compounds according to the invention may be used in diseases wherein the motility disturbances are associated with bicarbonate deficiency. This very often occurs in the cases of functional diseases, postprandially, relative to the average of healthy controls, in some parts of the stomach, where the environment of the lumen is often around pH 5 for a significantly longer time, therefore a decrease in the amount of the gastric acid in the stomach is unbeneficial, but bicarbonate should be added in the duodenum in view of its advantageous effect exerted first of all on the motility disturbances.

In addition, the compositions according to the invention may be used preferably together with active agents that need the restoration of the alkaline environment in the bowels to exert their effects and to be absorbed. The bicarbonate released from the composition according to the invention ensures the adequate pH environment in the bowels so that these agents could exert their activities. Such active agents are for example pancreatic and thyroid enzymes and bile acids, and also bi-functional minerals, metals and water-soluble vitamins may be taken into account.

FIGURES

Figure 2A:
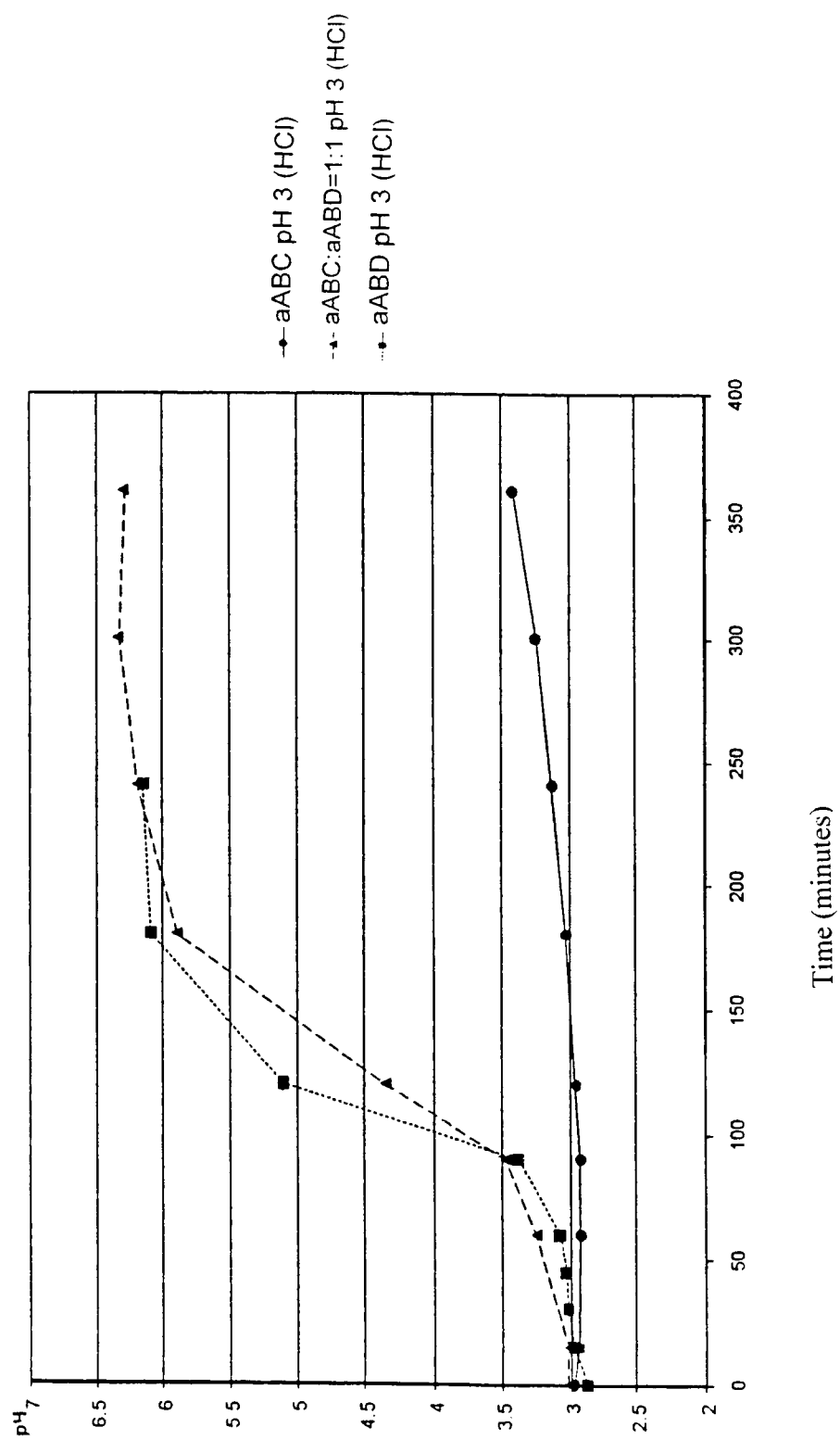

FIG. 1 shows the structure of the multilayer coatings of the microparticles according to the invention;

FIGS. 2a) to 2c) show the pH changes in the function of time on account of the active agent released from the microparticles in three solutions with diverse initial pH values, where the initial pH values were pH 3, pH 4.5 and pH 5.5 in FIGS. 2a), 2b) and 2c), respectively.

The examples below are disclosed solely by way of illustration; the scope of the invention is not limited to the contents of the examples.

EXAMPLES

Example 1

Preparation of a Composition Comprising MP-4.5 and MP-5.5 in Ratio 1:1.

1.1 Preparing MP Comprising $NaHCO_3$

In the preparation of 1000 g $NaHCO_3$ pellet core the following items are measured:

| | |
|---|---|
| $NaHCO_3$ | 809.0 g |
| Avicel PH 101 | 124.3 g |
| Kollidon VA 64 | 66.7 g |
| Ethanol (96%) | 336.0 g |

The components are homogenized in a high shear mixer at 900 rpm for 5 minutes. After homogenization, granulating material Kollidon VA64 in ethanol is sprayed at 900 rpm, with applying speed of 11.5 g/min, then pelletized at 900 rpm for 15 minutes. The resulted pellets are provided with multilayer coatings of aABC or aABD structure as described below.

1.2 Applying the Coating Layers

Preparation of coatinging solutions "a" and "A":

Eudragit powder is dissolved at room temperature by adding small portions to alcohol while stirring continuously. The dissolution period is 30 min. The agitation is carried out using a magnetic bar stirrer.

Coating "a": Solution of Eudragit E100 in ethanol
Composition of the Coating Solution:

| | |
|---|---|
| Eudragit E100 | 33 g |
| Ethanol 96% | ad 264 g |

Coating "A": Solution of Eudragit L100 in ethanol
Composition of the Coating Solution:

| | |
|---|---|
| Eudragit L100 | 33 g |
| Ethanol 96% | ad 264 g |

Coating parameters (for 150 g):

| | |
|---|---|
| Setting temperature: | 35° C. |
| Input air temperature: | 35° C. ± 3° C. |
| Output air temperature: | 29° C. ± 3° C. |
| Spraying air pressure: | 0.9 bar |
| Spraying speed: | 2.2 g/min |
| Speed of fluid air: | 80 m³/h |

Preparing dispersion "B":

30% polymer dispersion is mixed with water, then talc is dispersed therein while stirring continuously, after that the mixture is homogenized for 30 minutes.

Coating "B": Eudragit NE30D
Composition of the Coating Dispersion:

| | |
|---|---|
| Eudragit NE30D | 28.5 g |
| Talc | 4.25 g |
| Demineralized water | 28.5 g |

Coating parameters (for 150 g):

| | |
|---|---|
| Setting temperature: | 10° C. |
| Input air temperature: | 25° C. ± 2° C. |
| Output air temperature: | 20° C. ± 2° C. |
| Spraying air pressure: | 0.8 bar |
| Spraying speed: | 2.7 g/min |
| Speed of fluid air: | 50 m³/h |

Preparing dispersion "C":

HPMCP-50 powder is dissolved in the mixture of alcohol and water while stirring continuously.

Coating "C": HPMCP-50

Composition of the Coating Solution:

| | |
|---|---|
| HPMCP-50 | 20 g |
| Demineralized water | 36 g |
| Ethanol 96% | ad 200 g |

Coating parameters (for 150 g):

| | |
|---|---|
| Setting temperature: | 32° C. |
| Input air temperature: | 32° C. ± 2° C. |
| Output air temperature: | 28° C. ± 2° C. |
| Spraying air pressure: | 0.8 bar |
| Spraying speed: | 1.8 g/min |
| Speed of fluid air: | 100 m³/h |

Preparing dispersion "D":

Triethyl citrate is dispersed in water, then talc is dispersed in it while stirring continuously, after that they are mixed with 30% polymer dispersion, and the mixture is homogenized for 30 minutes.

Coating "D": Eudragit L30-D55

Composition of the Coating Dispersion:

| | |
|---|---|
| Eudragit L30-D55 | 159.0 g |
| Talc | 24.0 g |
| Triethyl citrate | 4.8 g |
| Demineralized water | ad 300.0 g |
| Weight of the pellet: | 114 g |

Coating parameters:

| | |
|---|---|
| Setting temperature: | 25° C. |
| Input air temperature: | 30° C. ± 2° C. |
| Output air temperature: | 23° C. ± 2° C. |
| Spraying air pressure: | 1 bar |
| Spraying speed: | 2.8 g/min |
| Speed of fluid air: | 50 m³/h |

The microparticles prepared according to the foregoing are mixed in ratio 1:1 and filled in gastrosolvent capsules, in portions of 1 g/capsule.

Example 2

Preparation of a Composition Comprising MP-4.5 and MP-5.5 in 2:1 Ratio.

MP-4.5 and MP-5.5 were prepared just as described in Example 1, and the two types of coated final micropellets are mixed in 2:1 ratio and filled in capsules.

Example 3

Dissolution Experiments

Dissolution experiments were carried out using standard rotating vane method according to the European Pharmacopoeia in 900 ml hydrochloride solution, pH 3, and phosphate blunting solutions, pH 4.5 and pH 5.5, respectively, on 37±0.5° C., at a mixing speed of 50 rpm.

In the experiment 2.0 g sample was measured (sodium bicarbonate content ~1.0 g) and the pH change was registered continuously using Microprocessor pH Meter pH 210 (Hanna Instruments, Woonsocket, US), measuring precision: ±0.01 pH value.

FIGS. 2a) to 2c) show the pH modifying effects of the samples in three solutions with diverse initial pH values, in the function of time, where the results of the experiments started at initial pH values of pH 3, pH 4.5 and pH 5.5 can be seen on FIGS. 2a), 2b) and 2c), respectively.

As it is shown on FIG. 2a), in the medium having initial pH 3 the acidic initial pH value remained essentially unchanged in the presence of MP-4.5, i.e. the sample coated with aABC, and in the presence of 1:1 mixture of MP-4.5/MP-5.5, i.e. the sample including coatings in ratio of aABC/aABD in 1/1 ratio, and the pH increased significantly only after 90 minutes, while in the presence of the sample coated with aABD, the pH value of the medium increased only slightly even after this period.

Figure 2B:
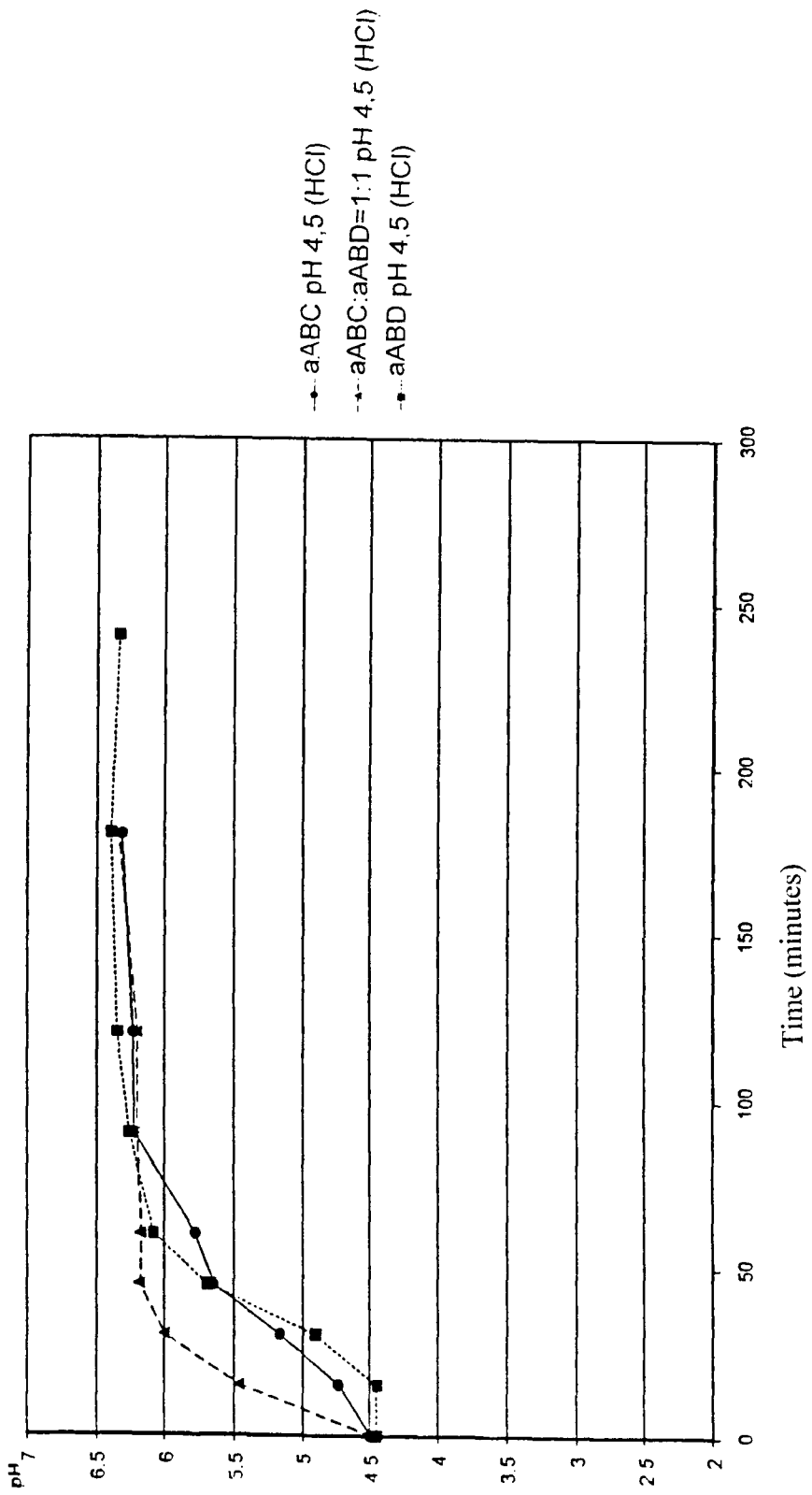

As it is shown on FIG. 2b), in the medium having initial pH 4.5 the mixture of particles with two types of coatings released bicarbonate most quickly (~30 min), it was followed by MP-4.5, and sodium bicarbonate was released from MP-5.5 lastly (90 min).

Figure 2C:
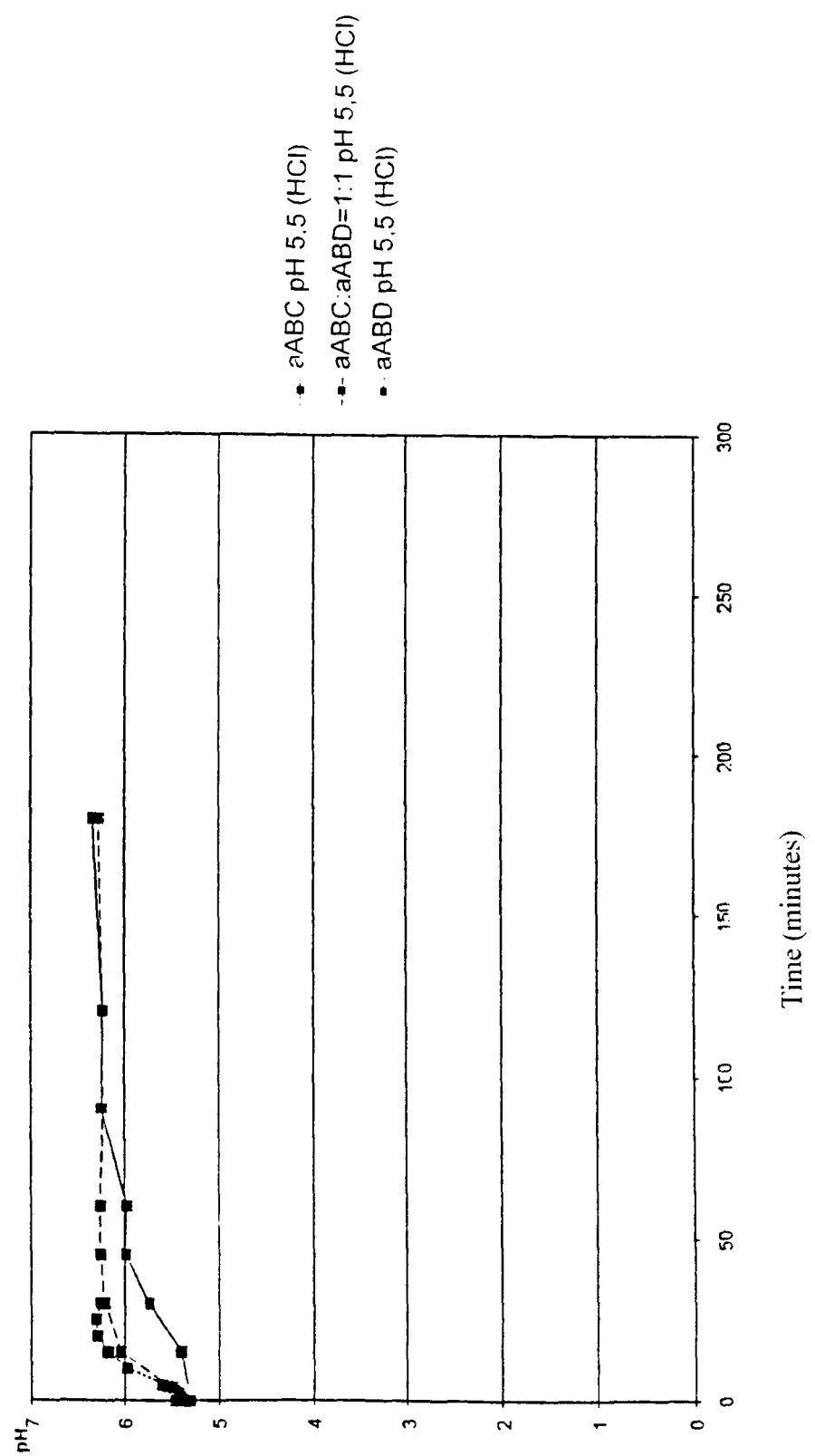

On FIG. 2c) the results obtained in the solution having initial pH 5.5 can be seen, where both the MP-4.5 and the mixed sample released sodium bicarbonate within 15 to 20 minutes, while MP-5.5 released sodium bicarbonate more slowly.

In the dissolution experiments of the 2:1 mixture of MP-4.5/MP-5.5 carried out under similar conditions we have got the following results (not shown in the figures).

In the medium having initial pH 4.5, the 2:1 mixture of particles with two types of coatings released bicarbonate within about 30 to 40 minutes, similarly to the 1:1 mixture.

In the medium of pH 5.5, the sample of 2:1 mixture released sodium bicarbonate within 15 minutes, which was a little faster than in the case of the sample of 1:1 mixture.

Firstly, the above results clearly show that both types of coatings fully hinder the release of sodium bicarbonate in the acidic environment of the stomach. This result is attained by the use of cationic protecting layer "a". Secondly, both MP-4.5 and the mixtures of MP-4.5/MP-5.5, that is, 1:1 and 2:1 mixtures provide adequate protection in the acidic environment of the stomach, but are able to decrease the hydrogen ion concentration at a higher pH value, which is of great importance in view of the long residence time in the duodenum.

The invention claimed is:

1. A pH dependent gradual release pharmaceutical composition for increasing the actual pH of the duodenum and the upper part of the jejunum by releasing sodium hydrogen carbonate there, which composition comprises a first and a second type of microparticles having multilayer enterosolvent coatings, wherein the first type of microparticles comprises
a cationic polymer coating insoluble above pH 5 (coating "a"), a polymer coating soluble at pH≥6 (coating "A"),
a pH-independent polymer coating (coating "B") and
an anionic polymer coating soluble at pH≥4.5 (coating "C"), and the second type of microparticles comprises
a cationic polymer coating insoluble above pH 5 (coating "a"),
a polymer coating soluble at pH≥6 (coating "A"),
a pH-independent polymer coating (coating "B") and
an anionic polymer coating soluble at pH≥5.5 (coating "D")

and the cores of microparticles comprising sodium hydrogen carbonate,
which first type of microparticles disrupts and releases sodium hydrogen carbonate at a threshold value of pH 4.5, and which second type of microparticles disrupts and releases sodium hydrogen carbonate at a threshold value of pH 5.5.

2. The composition according to claim 1, wherein the ratio of the first and second types of microparticles is 20/80 to 80/20.

3. The composition according to claim 1, which composition is filled in an gastrosolvent capsule.

4. The composition according to claim 1, wherein coating "a" comprises an aminoalkyl methacrylate copolymer, coating "A" comprises a copolymer of methacrylic acid and methacrylate, coating "B" comprises a copolymer of ethyl acrylate and methyl acrylate, coating "C" comprises hydroxypropyl methylcellulose phthalate and coating "D" comprises a copolymer of methacrylic acid and ethyl acrylate, and wherein the ratio of the first and second types of microparticles is 50/50.

5. The composition according to claim 1 for the treatment and prevention of disorders, wherein the actual amount of the bicarbonate available in the lumen of the small intestine is not sufficient for neutralizing the gastric acid or the acidic chymus and wherein the motility of the alimentary tract is disturbed.

6. A process for the preparation of the composition according to claim 1 characterized by preparing the particle cores from sodium hydrogen carbonate and commonly used pharmaceutical additives by alcoholic granulation under anhydrous conditions, then converting them to the first and second types of microparticles by consecutively applying the coating layers of the given type of microparticle, wherein coatings "a" and "A" are applied in the form of alcoholic solutions and coatings "B", "C" and "D" are applied in the form of aqueous solutions or dispersions, after that the diverse types of microparticles are mixed and optionally filled into gastrosolvent capsules.

7. A method for increasing the pH of the duodenum and the upper part of the jejunum of a patient, said method comprising orally administering the pharmaceutical composition of claim 1 to the patient and thereby releasing sodium hydrogen carbonate in said duodenum and/or said upper part of the jejunum of said patient upon the disrupting of both of said types of microparticles there.

8. The method of claim 7, wherein the actual amount of the bicarbonate available in the lumen of the small intestine of the patient is not sufficient for neutralizing the gastric acid or the acidic chymus and wherein the motility of the alimentary tract is disturbed.

9. The method of claim 7, wherein the pharmaceutical composition is administered in combination with pancreatic digestive enzymes.

10. The composition according to claim 1, wherein, upon disrupting, said first and second types of microparticles release sodium hydrogen carbonate without delay.

11. The composition according to claim 1, wherein the ratio of the first and second types of microparticles is in the range of about 1:1 to about 2:1, which composition releases sodium hydrogen carbonate at pH 4.5 within about 30 min and at pH 5.5 within 15 to 20 min.

12. The method of claim 7, wherein, upon disrupting, said first and second types of microparticles begin releasing sodium hydrogen carbonate without delay.

13. The method of claim 7, wherein the ratio of the first and second types of microparticles is in the range of about 1:1 to about 2:1, and wherein said composition completely releases the sodium hydrogen carbonate at pH 4.5 within about 30 min and at pH 5.5 within 15 to 20 min.

* * * * *